United States Patent [19]

Gaffney et al.

[11] Patent Number: 5,107,050
[45] Date of Patent: Apr. 21, 1992

[54] OLEFIN SKELETAL ISOMERIZATION

[75] Inventors: Anne M. Gaffney, West Chester; C. Andrew Jones, Newtown Square, both of Pa.

[73] Assignee: Arco Chemical Technology, L.P., Wilmington, Del.

[21] Appl. No.: 635,436

[22] Filed: Dec. 28, 1990

[51] Int. Cl.⁵ .......................... C07C 5/22; C07C 5/23
[52] U.S. Cl. ..................................... 585/671; 585/666
[58] Field of Search ................................ 585/671, 666

[56] References Cited

U.S. PATENT DOCUMENTS

| | | | |
|---|---|---|---|
| 4,503,282 | 3/1985 | Sikkenga | 585/671 |
| 4,864,068 | 9/1989 | Shamshoum | 585/514 |
| 4,882,038 | 11/1989 | Lok et al. | 585/666 |

Primary Examiner—Anthony McFarlane
Assistant Examiner—Nhat Phan
Attorney, Agent, or Firm—William C. Long

[57] ABSTRACT

The present invention relates to the improved skeletal isomerization of olefins over molecular sieve catalysts, the improvement comprising carrying out the skeletal isomerization at a temperature above 900° F.

2 Claims, No Drawings

OLEFIN SKELETAL ISOMERIZATION

BACKGROUND OF THE INVENTION

1. Field of the Invention

The present invention relates to the skeletal isomerization of olefins using molecular sieve catalysts wherein improved isomerization conversions and selectivities are achieved by carrying out the isomerization at temperatures in excess of 900° F. (482° C.) and preferably in excess of 925° F. (496° C.).

2. Description of the Prior Art

The skeletal isomerization of olefins using molecular sieve catalysts is a known reaction. See, for example, U.S. Pat. Nos. 4,567,029, 4,793,984, 4,683,217, 4,973,785, 4,882,038, 4,758,419, 4,500,651, 4,973,460 and the like. See also "Skeletal Rearrangement Reactions of Olefins, Paraffins and Aromatics over Aluminophosphate-Based Molecular Sieve Catalysts" by Regis J. Pellet, et al. ACS Symp. Ser. 1988, 368 p. 512–531.

Prior art patent references such as those listed above teach olefin skeletal isomerization at temperatures in the range 500° F. to 900° F. (260° C.–482° C.). Consistent with this, the literature article cited above provides data on the skeletal isomerization of 1-hexene at 650° F. (343° C.).

SUMMARY OF THE INVENTION

It has now been found that, contrary to the teachings in the prior art as illustrated by the references cited above, improved conversions and selectivities can be achieved in the vapor phase skeletal isomerization of olefins over molecular sieve catalysts where the isomerization is carried out at temperatures in excess of 900° F. and preferably in excess of 925° F.

DETAILED DESCRIPTION OF THE INVENTION

The catalysts which are used in carrying out the present invention are those molecular sieve catalysts taught in the art for this reaction. Generally speaking, the catalysts are of the aluminophosphate type known as non-zeolitic molecular sieves which are described, for example, in U.S. Pat. No. 4,740,650 at column 3, line 35 through column 48, line 9, the disclosure of which is incorporated herein by reference.

Particular preferred catalysts for use in the present invention are the medium pore-sized molecular sieves such as SAPO-11 and SAPO-31 and molecular sieves having the same general pore configuration. Especially preferred for practice of the invention are the molecular sieves which are described in U.S. Pat. Nos. 4,973,785 and 4,793,984 and which contain in addition to the framework oxide units of $AlO_2$, $SiO_2$ and $PO_2$ an oxide of a metal from the group consisting of arsenic, barium, boron, chromium, cobalt, gallium, germanium, iron, lithium, magnesium, manganese, titanium, vanadium and zinc. The most preferred catalysts employed in practice of the invention are the MgAPSO-11 and 31 sieves described in U.S. Pat. Nos. 4,882,038 and 4,758,419.

Olefins which are subjected to the skeletal isomerization reaction of the present invention are preferably normal olefins having 4 to about 20 carbon atoms, preferably alpha-monounsaturated olefins such as 1-butene, 1-pentene, 1-hexene and the like.

It is essential in practice of the present invention that the vapor phase isomerization reaction temperature be maintained in excess of 900° F., and preferably in excess of 925° F. Generally, the temperature should not exceed 1350° F. Normal isomerization pressures ranging from about atmospheric to 1,000 psig are conveniently employed. Isomerization space velocities of the order of about 1 to about 10,000 hr.$^{-1}$ WHSV are employed, preferably 10 to 1000 hr.$^{-1}$ WHSV.

The isomerization vapor feed can contain, in addition to the olefin to be isomerized, inert gas and/or steam although the use of these materials is not necessary or preferred.

Through practice of the present invention, surprisingly both the conversion and selectivity to the desired branched olefin isomers is substantially enhanced as a result of conducting the reaction at the designated temperatures as compared to operation at prior art temperatures. When using the preferred medium pore molecular sieve catalysts, catalyst coking is substantially avoided and the catalyst ca be used for extensive periods of time before reactivation is necessary. Catalyst reactivation can conveniently be achieved by known procedures including oxidation with molecular oxygen at elevated temperatures such as those employed in the isomerization.

In order to more clearly illustrate the invention, the following examples showing the skeletal isomerization of 1-butene are presented.

EXAMPLE

In accordance with this example, 1-butene was reacted over MgAPSO-31 prepared in accordance with U.S. Pat. No. 4,758,419 at various isomerization conditions. The results obtained are shown in the following table as are the conditions at which the isomerization was carried out. In each run, 1-butene in vapor phase was contacted with catalyst consisting of a mixture of 0.3 g. MgAPSO-31 and 0.7 g. alpha alumina, each 60–100 mesh, at the designated temperature and space velocity and at atmospheric pressure. In the following table the runs are grouped according to space velocity, not chronologically.

TABLE 1

| WHSV hr$^{-1}$ | Reaction Temp. °F. | 1-butene Conversion % | Selectivity to Isobutene % |
|---|---|---|---|
| 46 | 1112 | 41* | 74 |
| 46 | 1022 | 49 | 66 |
| 46 | 842 | 47 | 64 |
| 46 | 752 | 44 | 60 |
| 139 | 1022 | 40 | 81 |
| 139 | 932 | 35 | 77 |
| 139 | 842 | 31 | 71 |
| 139 | 752 | 22 | 67 |
| 23 | 752 | 59 | 49 |
| 23 | 662 | 37 | 49 |
| 12 | 662 | 60 | 43 |
| 12 | 572 | 49 | 31 |
| 93 | 1022 | 44 | 77 |

*Catalyst had been extensively used and was partially deactivated.

From the above table it can be seen that both the conversion and selectivity of the reaction of 1-butene to isobutene were improved by carrying out the isomerization at temperatures in excess of 900° F. as compared with runs having lower temperatures. In addition, for a given conversion, the selectivity of the reaction of 1-butene to isobutene is reduced as the isomerization temperature is lowered.

We claim:

1. In a process for the skeletal isomerization of a normal butene by reaction over a medium pore MgAPSO-31 molecular sieve catalyst, the improvement which comprises carrying out the skeletal isomerization at a temperature which is above 900° F.

2. In a process for the skeletal isomerization of a normal butene by reaction over a medium pore molecular sieve catalyst selected from the group consisting of SAPO-11, SAPO 31 and SAPO-11 and SAPO-31 also containing an oxide of a metal from the group consisting of arsenic, barium, boron, chromium, cobalt, gallium, germanium, iron, lithium, magnesium, manganese, titanium, vanadium and zinc, the improvement which comprises carrying out the skeletal isomerization at a temperature which is above 900° F.

* * * * *